Nov. 7, 1961 J. GABRIELSEN Plant Pat. 2,101
BLACK RASPBERRY PLANT
Filed Dec. 18, 1959
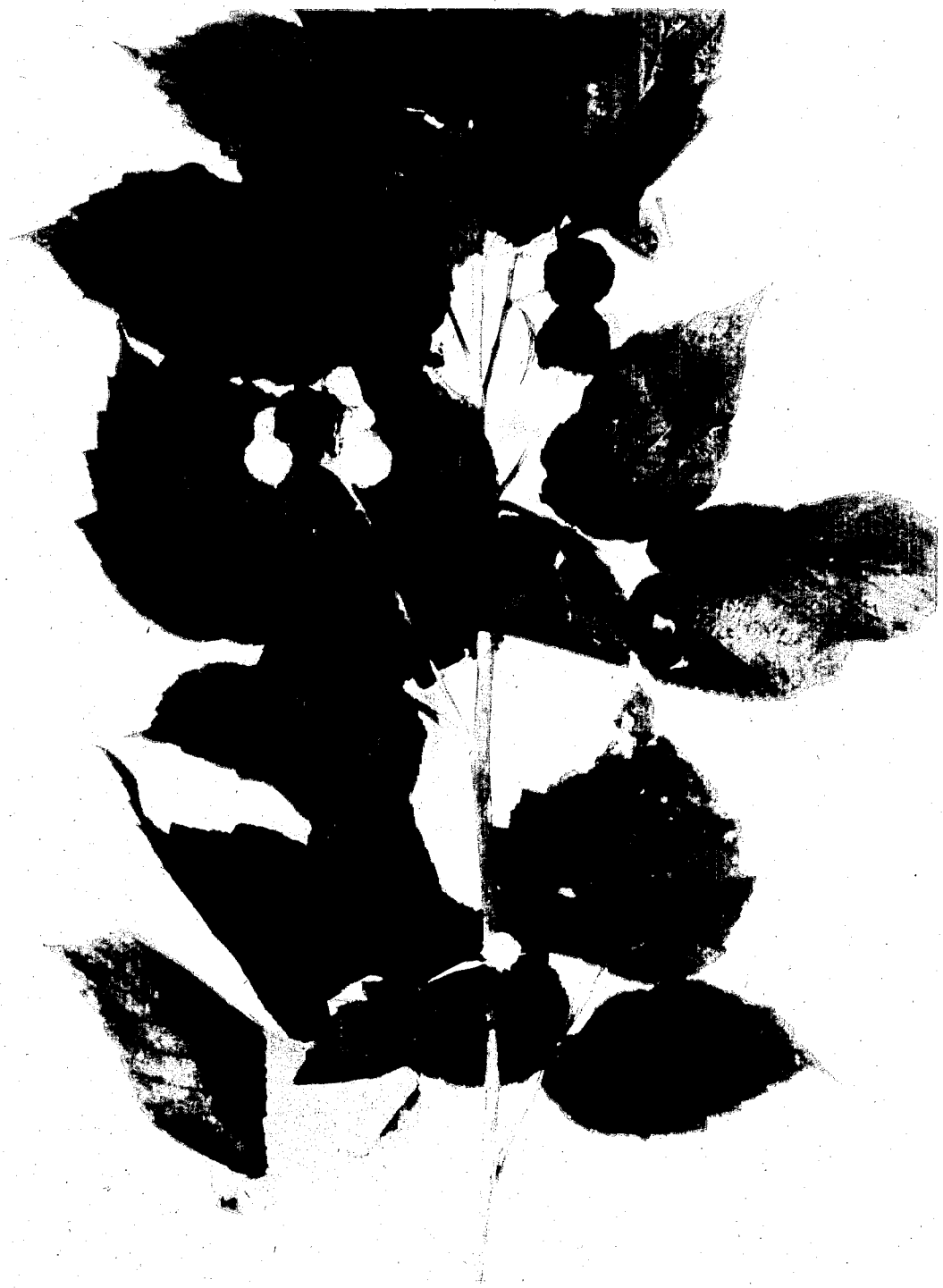

United States Patent Office

Plant Pat. 2,101
Patented Nov. 7, 1961

2,101
BLACK RASPBERRY PLANT

Joseph Gabrielsen, Graettinger, Iowa

Filed Dec. 18, 1959, Ser. No. 860,618
1 Claim. (Cl. 47—62)

This invention describes a new and different variety of black raspberry plant found by me as a cultivated seedling in my orchard at Graettinger, Iowa, in Palo Alto County. The seedling was produced by open pollination by "Cumberland" (unpatented), a commercial variety.

After ten years of observation and testing, my new variety has proved it is different and distinct from the "Cumberland" variety because of its much greater vigor, tallness and size of plant in growth, greater productivity, larger size of berry and resistance to drought, maturing a crop of large berries constant in size and producing from 3 to 4 quarts per plant while the fruit of the "Cumberland" and "Morrison" (unpatented) dried up on the canes before all had matured. The very good, sprightly flavor of the berry differs from the "Cumberland" variety in this pronounced or sprightly flavor and because of the small seeds, the berry is plump and without objectionable seediness. The new variety is distinctly different from other varieties; it has definite qualities and characteristics in appearance from other varieties in plant growth and berries that is superior to other plants that I know of. The following are the desirable and outstanding qualities or characteristics of my new variety which make it a valuable contribution to the commercial and home grower:

(1) The especial sturdiness, vigor and drought resistance and productivity of the plant.

(2) The comparatively large size of the fruit relatively constant through the season and its firmness and freedom from crumbling.

(3) The plump, attractiveness of the fruit with small seeds and the very good sprightly flavor.

This new variety has been asexually reproduced by layering in Palo Alto County and discloses that the following distinct characteristics hold true to form and remain established and transmissible through succeeding propagation of plants.

The enclosed drawing shows typical specimens of fruit and foliage of my new variety.

The following is a description of my new variety as to identification. Terms in color refer to the indicated colors as found in "Color Standards and Nomenclature," by Robert Ridgway.

Parentage: Seedling from open pollination of "Cumberland."

Propagation: Remains true to form and retains distinctive characteristics through succeeding generations.

Harvest: First picking in Palo Alto County, Iowa, July 10, 1960, last July 24, 1960.

The characteristics noted from my new variety grown and tested in Palo Alto County, Iowa, are as follows:

The plant:

*Growth.*—Vigorous, tall, distinctive.

*Crown.*—Large, sturdy, branched usually 4 to 5 canes.

*Root.*—Vigorous.

Leaves: Close together, many, large. Petiole, 0.12 inch diameter at base, strong; 1.62 inches from lower to upper leaflet. Color, upper surface, Spinach Green, Plate V, color 29 GG–Y, tone M. Lower surface, Pea Green, Plate XL, color 29'''' GG–Y, tone B. Pubescence, lacking. Leaflets, trifoliate. Size, central leaflet, 4 inches by 4½ inches; side leaflet, 4 inches by 3 inches. Veins prominent on underside. Midrib very prominent.

Attached to leaf blade only on 90 degrees in cross section. Secondary veins also prominent, also tertiary veins on lower lobe of lower leaflets. Shape, ovate, tapering to acute point at distal end. Serrations, coarsely and finely serrate; 4 and 5 serrations per coarse serration, 26 coarse serrations per central leaflet. Average 19 serrations per lower leaflet.

Canes: Tall, stout; .6 to 1.0 inch in diameter at base. Color, Parrot Green, Plate VI, color 31 Y–G, tone K, with thorns of the same color. Surface, no pubescence, glabrous. Thorns; spines on Prima canes infrequent at time of fruiting, about 4 per inch. Floricanes, hard spines .121 inch long. No regularity of pattern, 51 per linear inch.

Hardiness: Withstood −24° F. without injury.

Fruit: Examined July 12, 1960. Berries range from 12 to 20 berries per shoot.

*Size.*—Large, uniform, constant through harvest. Length, ⅝ inch, traverse ⅞ inch, with primary berries measuring 1 inch. Average size of berries, 1.52 grams; larger than "Bristol" (unpatented) variety.

*Form.*—Rounded truncate, tapering slightly, uniform, rounded apex, irregular base.

*Cavity.*—Small, wedge shaped, narrow funnel shaped. Color, Lilac Gray, Plate LII, color 59'''' Violet, tone F.

*Druplets.*—Berries average 85. About 3/32 inch in diameter, medium large, irregularly round with definite suture from base.

*Receptacle.*—Small, length 3/16 inch, diameter, 3/16 inch. Color, Straw Yellow, Plate XVI, color 21'.O–YY, Tone D.

*Color*—Dull Purplish Black, glabrous, Plate L, color 65'''' RR–V, tone M. Before ripening the berries are red (ordinary dictionary definition).

*Stamens.*—Length, ⅛ inch.

*Sepals.*—5 in number, length ⅜ inch, width at base 5/32 inch abruptly tapering to a sharp point; smooth. Color, Pod Green, Plate XLVII, color 29''''.GG–Y, tone B.

*Fruit stems.*—Spiny, ⅝ inch long to 1⅝ long.

*Seed.*—Small, .080 inch length, .050 inch width, .025 inch thickness. Pitted surface, varied color but mostly Plum Purple, Plate XXIV, color 57* VB–V, tone M.

*Flesh.*—Firm, juicy. Color, Plum Purple, Plate XXIV, color 57* VB–V, tone M.

*Flavor.*—Sprightly.

*Quality.*—Very good.

*Harvest.*—7 days after "Cumberland," later than "Bristol" (unpatented).

*Use.*—Market, dessert, freezing and canning. Stands up well for shipping.

The berries are out in the open and separate readily from the torus.

Type of soil grown in: Black sandy loam and clay loam.

I claim:

A new and distinct variety of black raspberry plant, as herein shown and described, characterized particularly as to novelty by the unique combination of large and vigorous growth, very productive fruit bearing habit, larger size of fruit, delightful flavor, firmness and smallness of the seed thereof.

References Cited in the file of this patent

UNITED STATES PATENTS

P.P. 1,494 Stouffer ..... July 3, 1956
P.P. 1,567 Loretto ..... Feb. 19, 1957